(12) United States Patent
Rich

(10) Patent No.: US 6,261,314 B1
(45) Date of Patent: Jul. 17, 2001

(54) THERMAL TREATMENT PACK AND CORRESPONDING RETAINER MEMBER AND METHODS OF APPLYING THERMAL TREATMENT

(76) Inventor: Patricia Lyn Rich, 4085 Calle Isabella, San Clemente, CA (US) 92672

( * ) Notice: Subject to any disclaimer, the term of this patent is extended or adjusted under 35 U.S.C. 154(b) by 0 days.

(21) Appl. No.: 09/378,347

(22) Filed: Aug. 20, 1999

(51) Int. Cl.[7] .................................................. A61F 7/00
(52) U.S. Cl. .......................... 607/109; 607/112; 607/114
(58) Field of Search ................................. 607/108, 109, 607/110, 112, 114

(56) References Cited

U.S. PATENT DOCUMENTS

| | | |
|---|---|---|
| D. 265,422 | 7/1982 | Howe . |
| D. 290,512 | 6/1987 | Bagg et al. . |
| 4,190,054 * | 2/1980 | Brennan ............................... 128/402 |
| 4,586,506 | 5/1986 | Nangle . |
| 4,742,827 | 5/1988 | Lipton . |
| 4,765,338 | 8/1988 | Turner et al. . |
| 4,854,319 | 8/1989 | Tobin . |
| 5,020,536 * | 6/1991 | Keen .................................... 128/402 |
| 5,020,711 | 6/1991 | Kelley . |
| 5,109,841 | 5/1992 | Hubbard et al. . |
| 5,119,812 | 6/1992 | Angelo . |
| 5,129,391 * | 7/1992 | Brodsky et al. ..................... 128/380 |
| 5,188,103 | 2/1993 | Smith . |
| 5,356,426 | 10/1994 | Delk et al. . |
| 5,395,400 | 3/1995 | Stafford et al. . |
| 5,409,500 | 4/1995 | Dyrek . |
| 5,628,772 | 5/1997 | Russell . |
| 5,643,336 | 7/1997 | Lopez-Claros . |
| 5,697,962 | 12/1997 | Brink et al. . |
| 5,837,004 | 11/1998 | Lavore . |
| 5,984,951 * | 11/1999 | Weiss et al. ......................... 607/109 |
| 6,093,202 * | 7/2000 | Dyken et al. ........................ 607/109 |

OTHER PUBLICATIONS

Dura–Kold Brochure.
P. 6 of FeelGood Summer 1988 Catalog, 2895 West Oxford Avenue, Suite #1, Englewood, CO 80110.
Advertisement for CP2 Cold Pad.
PI Medical Advertisement, Apr. 1998.
Polar Pad Advertisement.

* cited by examiner

Primary Examiner—Linda C. M. Dvorak
Assistant Examiner—Jocelyn Debra Ram
(74) Attorney, Agent, or Firm—Knobbe, Martens, Olson & Bear LLP

(57) ABSTRACT

A thermal treatment pack and corresponding retainer apparatus that provide not only a desirable thermal source, but also a highly configurable retainer apparatus. According to one embodiment, the thermal source includes frozen peas stored in transparent bags. The transparent bags are selectively attachable through hook-and-loop fasteners. According to the preferred embodiment, the retainer apparatus includes two washable cloth strips. The cloth strips include hook-and-loop fasteners for attaching the transparent bags to the retainer apparatus.

9 Claims, 6 Drawing Sheets

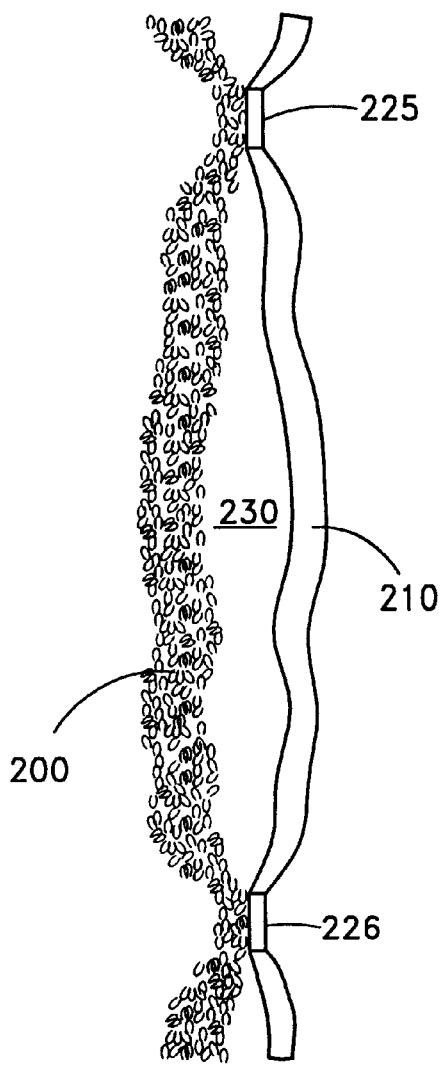
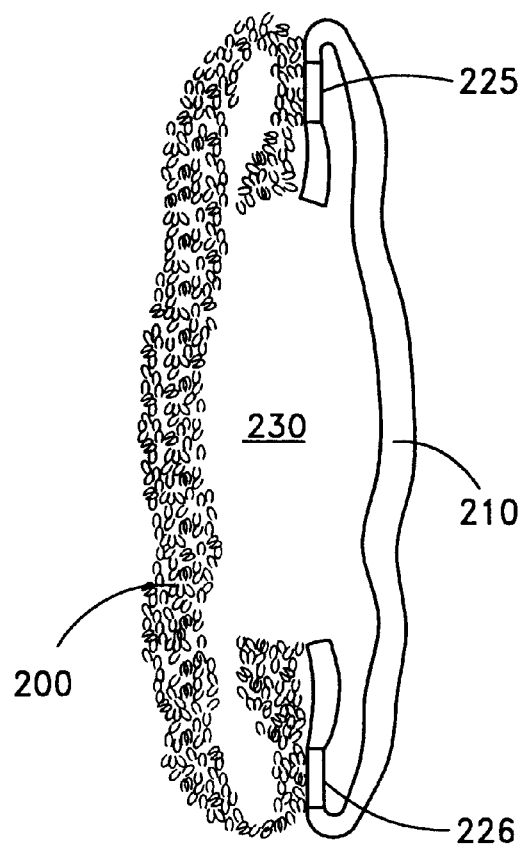
FIG. 4E
FIG. 4F

THERMAL TREATMENT PACK AND CORRESPONDING RETAINER MEMBER AND METHODS OF APPLYING THERMAL TREATMENT

BACKGROUND OF THE INVENTION

1. Field of the Invention

The present invention relates in general to thermal treatment of tissue, and in particular to postoperative thermal treatment of the facial area.

2. Background

The benefits of thermal treatment to injured or damaged tissue or to relieve postoperative pain and swelling are well known. In fact, there exists a multitude of devices designed to apply thermal treatment to various parts of the human body for various differing aliments. Some prior art thermal treatment devices include a variety of ice bags permanently stitched to a face harness or mask. These thermal treatment devices require removal of the face harness when the temperature of the ice bag rises.

In an attempt to make ice bags easier to exchange, some thermal treatment devices include a limited number of hook-and-loop fasteners, such as Velcro. Corresponding fasteners are attached to the ice bags such that the ice bags can be easily attached and detached from the limited number of hook-and-loop fasteners. However, these thermal treatment devices are also unsatisfactory and are characterized as being very intrusive, either blocking thermal treatment, and/or limiting thermal treatment to the area having the hook-and-loop fasteners.

Another approach has been to use thermal treatment devices having sectioned harnesses. For example, these thermal treatment devices may be divided into a neck section, a chin section, a facial section, and a head section. Each section typically attaches to the next and each section is individually frozen. Sectioned thermal treatment devices are characterized as being poorly configurable to the contours of the face for at least two reasons. First, as mentioned, each entire section is frozen, making that section very difficult to adjust to a given face. Second, partial coverage in a given section is usually not possible. For example, if the thermal treatment device has a removable facial section, treatment of only one side of the face is not possible. Either the removable facial section is attached, thereby treating the entire face, or the removable facial section is detached, thereby treating none of the face.

SUMMARY OF THE INVENTION

The invention provides a retainer member and thermal treatment pack that combines a desirable thermal source and retainer to achieve a flexible configuration and patient mobility.

The preferred embodiment of the invention comprises an improved retainer member formed by a horizontal and a vertical strip of lightweight washable cloth. Each strip is connected with hook-and-loop fasteners located along an extended length of the strip to create a lightweight retainer upon which thermal treatment bags are attached. Each such thermal treatment bag is selectively fastenable along a substantial portion of the retainer by mating hook-and-loop fasteners.

A significant feature of the preferred embodiment of the invention is that it advantageously provides for fastening and removal of multiple thermal treatment packs without requiring the removal of the retainer member. Moreover, the pattern of the hook-and-loop fasteners facilitates easy positioning in a multitude of facial locations while providing stability when, for example, a patient must recuperate in an upright position. In addition, the hook and loop fasteners advantageously provide for selective fastening of multiple thermal treatment packs, thereby enabling both complete and partial facial coverage from different horizontal and vertical positions. As a result, thermal treatment devices constructed in accordance with the preferred embodiment apply effective thermal treatment for a wide range of uses. For example, while one postoperative patient needing thermal treatment may be unconscious or bed-ridden, another patient may simply have aches and pains. The preferred embodiment provides for the sturdiness needs of the first patient and the mobility needs of the second.

Another feature of the preferred embodiment is that it is configurable to the many differing contours of the face, while still allowing for some degree of mobility for the patient. According to one embodiment, the thermal source includes frozen peas stored in transparent bags. The transparent bags are selectively attachable through hook-and-loop fasteners. Use of frozen peas as an thermal source advantageously provides desired cooling temperatures while also providing desired immediate molding to the contours of a treated area. Frozen peas are also light in weight so that stress on the patient is minimized when the thermal treatment pads are retained over a sensitive portion of the face or other body portion.

For the purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

Other aspects and advantages of the invention will be apparent from the detailed description below and the appended claims.

BRIEF DESCRIPTION OF THE DRAWINGS

The present invention is described in more detail below in connection with the attached drawings, which are meant to illustrate and not to limit the invention, and in which:

FIG. 4E is an enlarged cross-sectional view during fabrication of the horizontal strip illustrated in FIGS. 4A and 4B;

FIG. 4F is an enlarged cross-sectional view of the completed horizontal strip in FIGS. 4A and 4B prior to attachment of the length of loop material 150;

DETAILED DESCRIPTION OF THE PREFERRED EMBODIMENTS

While illustrated in the context of applying thermal treatment packs to a face of a user, the skilled artisan will find application for the disclosed thermal treatment pack and corresponding retainer apparatus in a wide variety of contexts. For example, the thermal treatment pack could be adapted for use with other retainer apparatuses, or vise versa. In addition, the thermal treatment packs and the retainer apparatus could be modified to treat other areas of the body, such as the breast after breast surgery.

Figure 1:
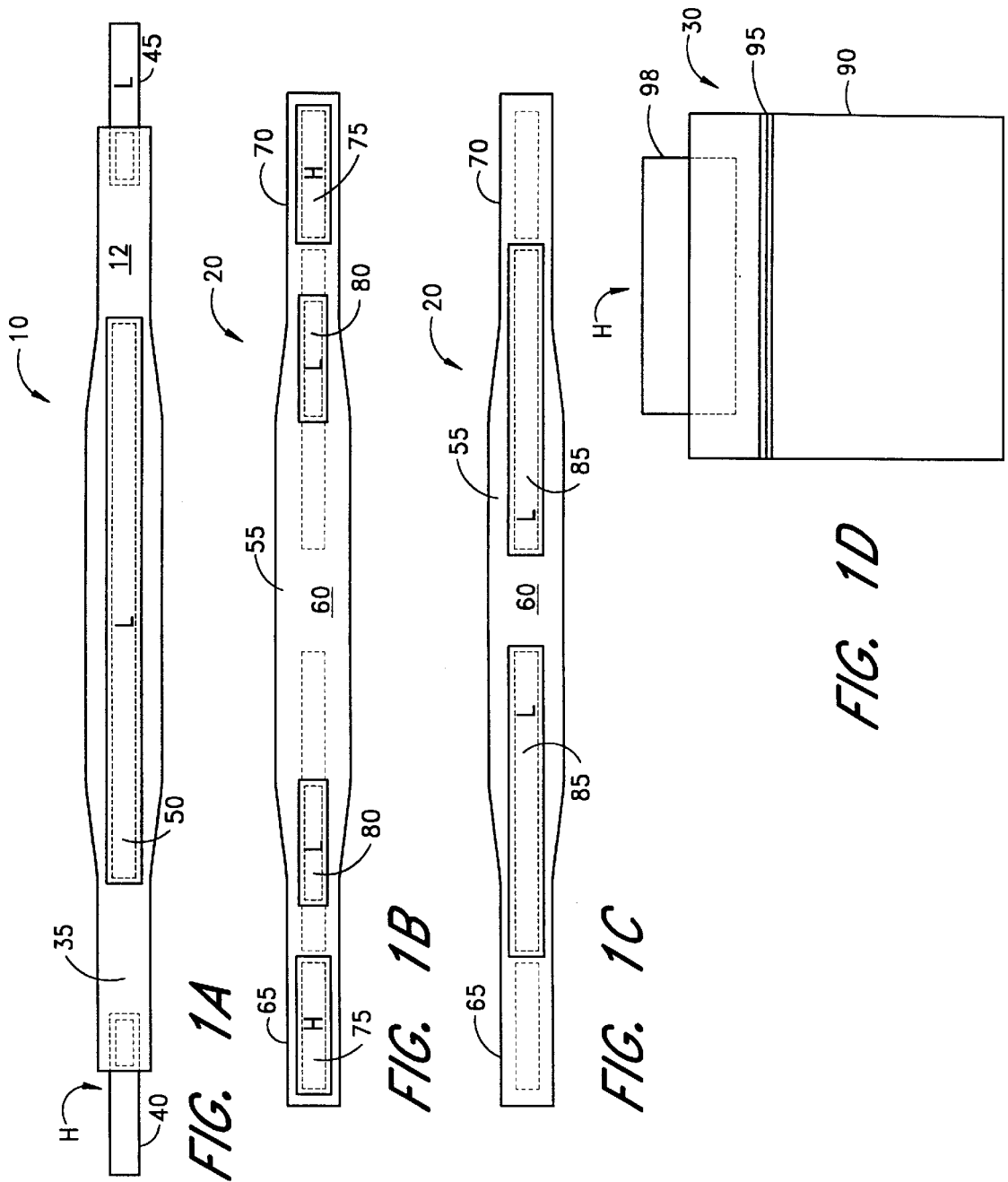
FIG. 1A is an elevational view illustrating the front side of the horizontal strap of the retainer member, according to a first embodiment of the invention.
FIG. 1B is an elevational view illustrating the front side of a vertical strap of the retainer member, according to the first embodiment of the invention.
FIG. 1C is an elevational view illustrating the back side of the vertical strap of FIG. 1B.
FIG. 1D illustrates a thermal treatment pack, according to an embodiment of the invention.
Figure 2:
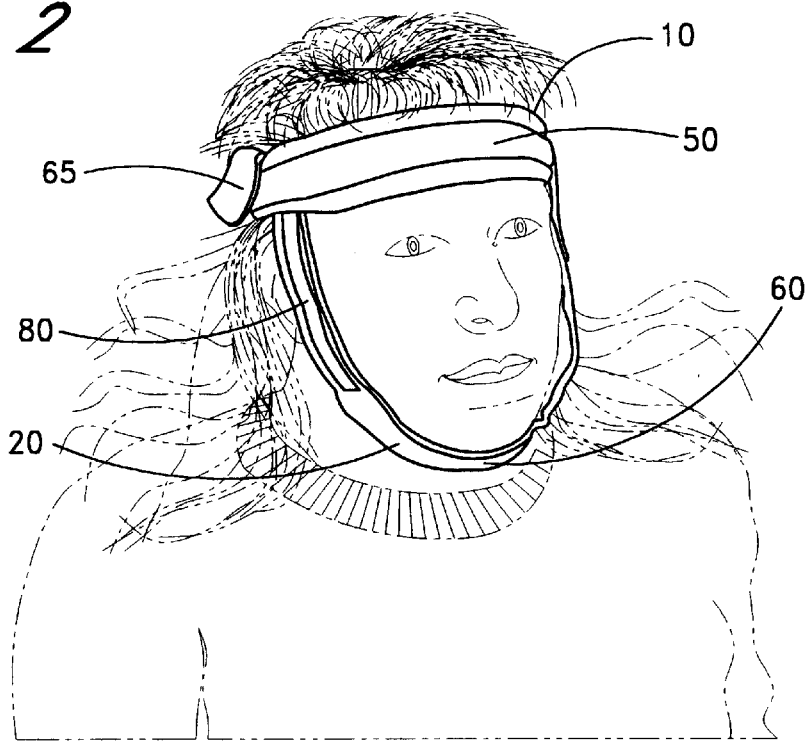
FIG. 2 illustrates the first embodiment of the invention in the operative position on the face of a user.
Figure 3:
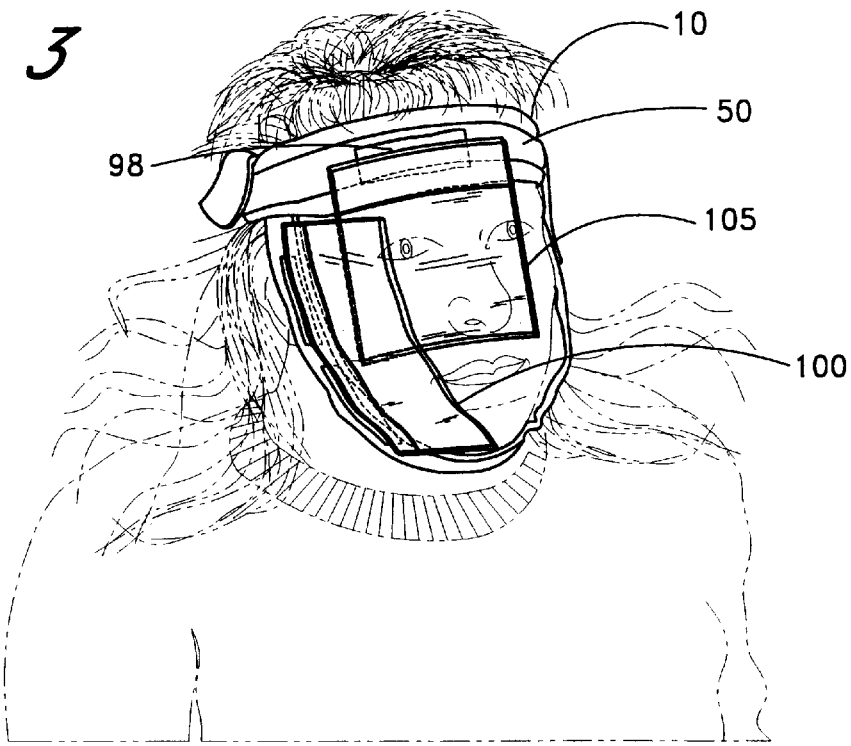
FIG. 3 illustrates the retainer member, according to the first embodiment of the invention, and two attached thermal treatment packs, all in the operative position on the face of the user.

The retainer member of the embodiment shown in FIGS. 2 and 3 comprises a horizontal strap 10 and vertical strap 20. Advantageously, as shown, this retainer member frames the patient's face from the forehead to below the chin. As shown in FIG. 1D, thermal packs 30 are fastenable to this member in a variety of facial locations.

Referring to FIG. 1A, the horizontal strap 10 advantageously includes a cloth strip 35 made from washable cloth material. The cloth strip 35 includes a left fastener 40 attached to the left end of the cloth strip 35 and a right fastener 45 attached at the right end thereof. Advantageously, the left and right fasteners, 40 and 45, comprise corresponding hook-and-loop type fasteners. Thus, for example, the left fastener 40 is shown with hook material on the back of the side shown in FIG. 1A. FIG. 1A indicates the hook material with the capital letter "H." On the other end, the right fastener 45 comprises loop material on the front side 12 of the horizontal strap 10 as shown in FIG. 1A. FIG. 1A indicates the loop material with the capital letter "L." Therefore, the left and right fasteners, 40 and 45, are configured to connect with each other and secure the horizontal strap 10 to an upper portion of the head area of the user as shown in FIG. 2.

It will be understood that FIGS. 1A–1D, 4A–4D and 6 indicate whether types of hook-and-loop fasteners are hook material or loop material, with the capital letters "H" and "L" respectively. It will also be understood that a skilled artisan would recognize each material could be substituted for the other.

The cloth strip 35 further includes a thermal pack fastener 50. According to one embodiment, the thermal pack fastener 50 comprises loop material running substantially the entire length of the horizontal strap 10. The thermal pack fastener 50 attaches to the cloth strip 35 on the front side 12 of the horizontal strap 10. Accordingly, when the left and right fasteners, 40 and 45, are connected such that the horizontal strap 10 is secured to the upper portion of the user's head, the thermal pack fastener 50 outwardly from the user's head as shown in FIG. 2.

By employing the horizontal strap 10, the material facing the upper portion of the user's head will be the soft, washable, cloth strip 35, while the material facing away from the user's head will comprise the material of the thermal pack fastener 50. This arrangement creates a comfortable, secure, versatile, non-intrusive anchor for the thermal treatment packs 30 shown in FIG. 1D, 3 and 5.

Further, it will be understood that a wide variety of fasteners can be used for the left and right fasteners, 40 and 45, and the horizontal bag fastener 50. In particular, the left and right fasteners, 40 and 45 remain fastened during the time the user wears the retainer apparatus, and therefore, could be any conventional fastener known to a skilled artisan. In the preferred embodiments, the thermal pack fastener 50 will be the type of fastener that is easily and readily unfastenable, thereby allowing items to be conveniently fastened and unfastened without undue motion or stress being applied to the horizontal strap 10.

FIG. 1B illustrates the front of the vertical strap 20, i.e., the side of the vertical strap facing outwardly from the user's head. According to one embodiment, the vertical strap 20 comprises a cloth strip 55 made from any conventional washable cloth material. The cloth strip 55 includes a chin area 60 substantially in the center thereof. The chin area 60 will be further discussed below. The cloth strip 55 also has a left end 65 and a right end 70. According to one embodiment, the left and right ends, 65 and 70, have a width slightly reduced from that of the majority of the cloth strip 55. In addition, the left and right ends, 65 and 70, include end fasteners 75 made of hook material. The remaining portions of the cloth strip 55 include middle fasteners 80 made of loop type material. One middle fastener 80 is between the left end 65 and the chin area 60, while the other middle fastener 80 is between the chin area 60 and the right end 70.

It will be understood that the skilled artisan would recognize a variety of different patterns for the above-mentioned side of the vertical strap 20. For example, the vertical strap 20 could have substantially reduced end widths, or simply uniform widths throughout. Furthermore, this side of the vertical strap 20 could have a larger chin area 60, or simply no chin area 60 at all.

FIG. 1C illustrates the back of the vertical strap 20, i.e., the side facing the user's head. According to one embodiment, this side of the vertical strap 20 includes the chin area 60. This side of the chin area 60 does not have any fastener material thereon, such that the soft, washable, cloth strip 55 rests against the user's chin. Thus, the chin area 60 advantageously avoids being uncomfortable or irritating to the user.

The side of the vertical strap 20 illustrated in FIGURE iC further includes thermal pack fasteners 85. These fasteners 85 extend from the left end 65 to the chin area 60 and from the right end 70 to the chin area 60. According to one embodiment, the thermal pack fasteners 85 are loop fasteners.

It will be understood that the skilled artisan would recognize a variety of different patterns for the side of the vertical strap 20 illustrated in FIG. 1B and 1C. For example, because substantial loop material exists on the front side of the vertical strap 20 as the middle fasteners 80, the loop material 85 on the back of the vertical strap 20 could be avoided. In this embodiment, the thermal treatment packs 30 would fasten to the middle fasteners 80 and only the soft, washable cloth strip 55 would face the user's head.

FIG. 1D illustrates one embodiment of a thermal treatment pack 30 according to the invention. The thermal treatment pack 30 advantageously includes a transparent bag 90 having a resealable fastener 95 such as those commonly found on food storage bags. The thermal treatment pack 30 also includes a fastener strip 98 attached above the resealable fastener 95. According to one embodiment of the invention, the fastener strip 98 includes hook material configured to fasten to any of the loop material found on the horizontal and vertical straps, 10 and 20, e.g., fasteners 50, 80, and 85. In another embodiment not shown, the fastener strips 98 are located along the top and side of bag 90.

The resealable fastener 95 on the transparent bag 90 allows for the thermal source to be placed inside the transparent bag 90. According to one embodiment, the thermal source comprises frozen peas. Frozen peas are advantageously small enough to immediately conform to the many contours of the human face. They are lighter in weight than most thermal sources. Furthermore, frozen peas advantageously do not have the extreme cold that other thermal sources may carry. Thus, the frozen peas inside the transparent bag 90 can be applied directly to the affected tissue without concern of harming the tissue with extreme temperatures.

Figure 5:
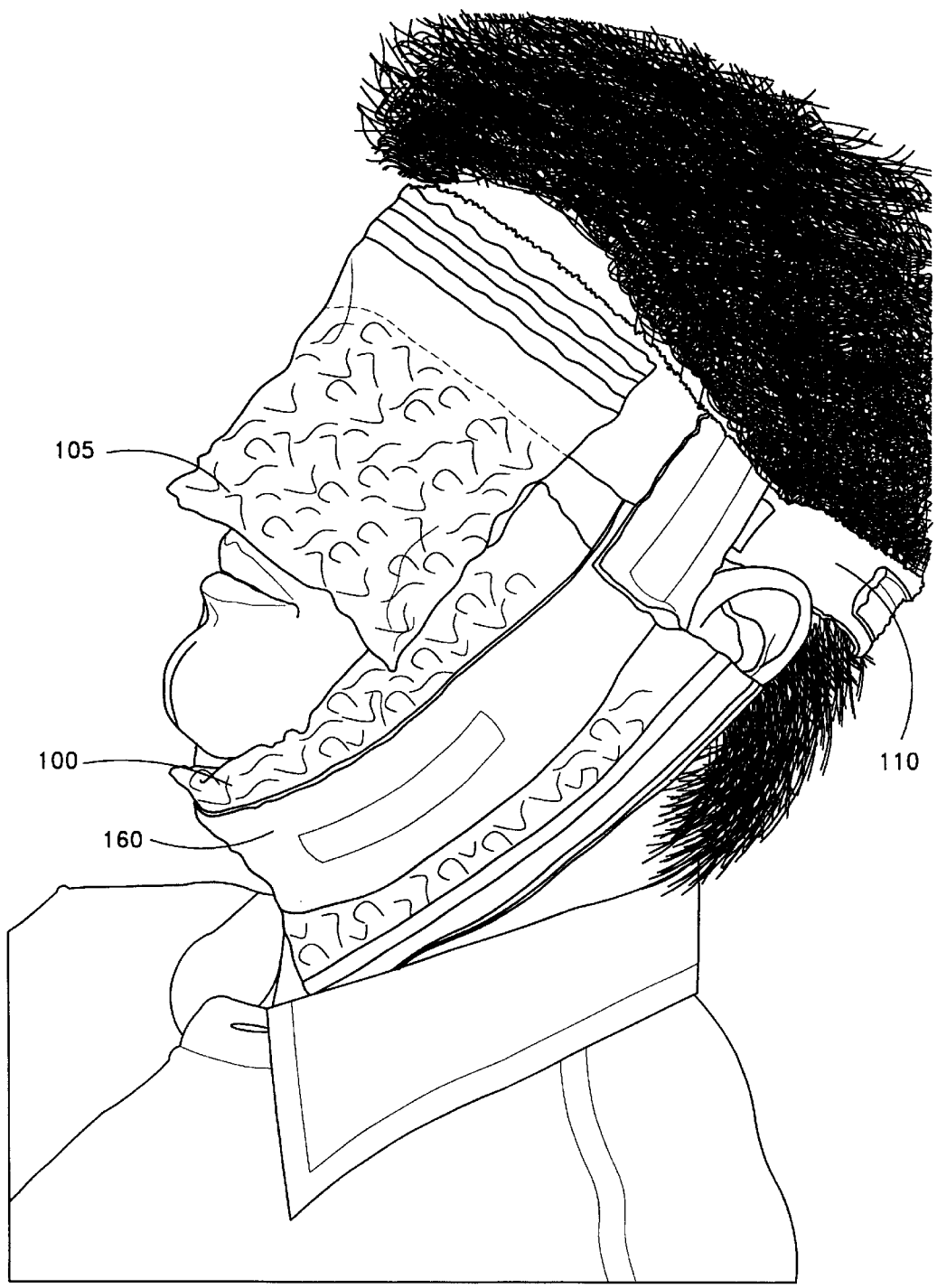
FIG. 5 illustrates the retainer member, according to the second embodiment of the invention, in the operative position on the face of a user with two thermal thread treatment bags.

As shown in FIG. 1D, 3 and 5, it will be understood that the thermal treatment pack 30 can be of practically any size and any other shape. Furthermore, the fastener strip 98 can attach to any side of the transparent bag 90. It will also be understood that the transparent bag 90 can include a wide variety of thermal sources, examples being frozen corn, synthetic materials, or the like. In addition, the transparent bag 90 can hold ice chips, refreezable thermal sources, thermal sources which may be heated to a predetermined temperature or any other thermal source known to a skilled artisan.

FIG. 2 illustrates the retainer member comprising the horizontal and vertical straps, 10 and 20, on the patient's head, in their operative position. As shown, the horizontal strap 10 attaches around the upper portion and over the forehead of the user's head. The horizontal strap 10 is secured by fastening the left and right fasteners, 40 and 45, together. The vertical strap 20 threads between the user's head and a portion of the horizontal strap 10 on the left side of the user. The left end 65 then folds over the horizontal strap 10. Because the end fastener 75 comprises hook material, the end fastener 75 may attach to both the middle fastener 80 of the vertical strap 20 and fastener 50 of the horizontal strap. The chin area 60 wraps around the user's chin and the right end 70 of the vertical strap 20 attaches in a similar manner to that described with reference to the left end 65.

Figure 4A:
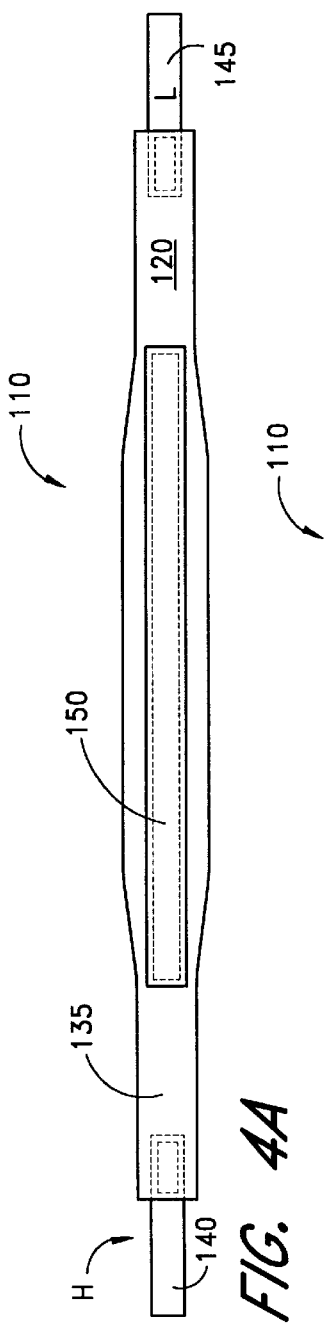
FIG. 4A is an elevational view illustrating the front side of the horizontal strap of the retainer member, according to a second embodiment of the invention.
Figure 4B:
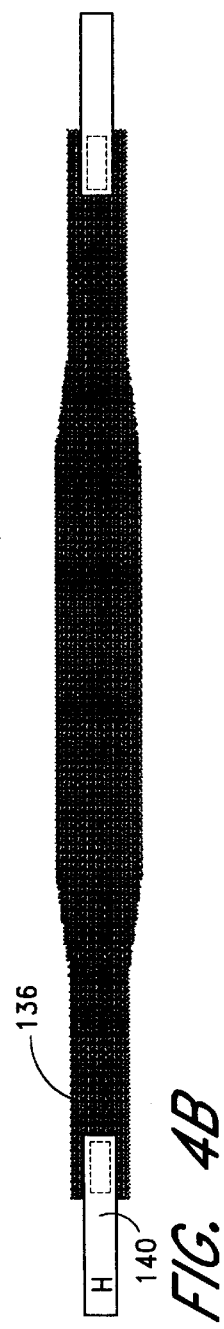
FIG. 4B is an elevational view illustrating the back side of the horizontal strap of the retainer member, according to the second embodiment of the invention.

Another embodiment of the invention is illustrated in FIGS. 4A–4D. As shown in FIG. 4A, this embodiment includes a horizontal strap 110 having a plain front surface 135 and a pile back surface 136 advantageously formed from terry cloth as described in more detail below. As in the embodiment of FIG. 1A–1C, the cloth strip 135 includes a left fastener 140 attached to the left end of the cloth strip 135 and a right fastener 145 attached at the right end thereof.

Advantageously, the left and right fasteners, 140 and 145, comprise corresponding hook-and-loop type fasteners. Thus, for example, the left fastener 140 is shown with hook material on the back side shown in FIG. 4A. FIG. 4A indicates the hook material with the capital letter "H." On the other end, the right fastener 45 comprises loop material on the front side 120 of the horizontal strap 10 as shown in FIG. 1A. FIG. 1A indicates the loop material with the capital letter "L." Therefore, the left and right fasteners, 40 and 45, are configured to connect with each other and secure the horizontal strap 110 to an upper portion of the head area of the user as shown in FIG. 5.

It will be understood that FIGS. 4A–4D indicate whether types of hook-and-loop fasteners are hook material or loop material, with the capital letters "H" and "L" respectively. It will also be understood that a skilled artisan would recognize that each material could be substituted for the other.

The cloth strip 135 further includes a thermal pack fastener 150. According to one embodiment, the thermal pack fastener 150 comprises loop material running substantially the entire length of the horizontal strap 110. The thermal pack fastener 150 attaches to the cloth strip 135 on the front side 120 of the horizontal strap 110. Accordingly, when the left and right fasteners, 140 and 145, are connected such that the horizontal strap 110 is secured to the upper portion of the user's head, the thermal pack fastener 150 faces outwardly from the user's head as shown in FIG. 5.

By employing the horizontal strap 110, the material facing the upper portion of the user's head will be the soft, washable, terry cloth strip 136, while the material facing away from the user's head will include the material of the horizontal bag fastener 150. This arrangement creates a comfortable, secure, versatile, non-intrusive anchor for the thermal treatment packs 30 shown in FIG. 1D.

Further, it will be understood that a wide variety of fasteners can be used for the left and right fasteners, 140 and 145, and the horizontal bag fastener 150. In particular, the left and right fasteners, 140 and 145 remain fastened during the time the user wears the retainer apparatus, and therefore, could be any conventional fastener known to a skilled artisan. In the preferred embodiments, the horizontal bag fastener 150 will be the type of fastener that is easily and readily unfastenable, thereby allowing items to be conveniently fastened and unfastened without undue motion or stress being applied to the horizontal strap 110.

Figure 4C:
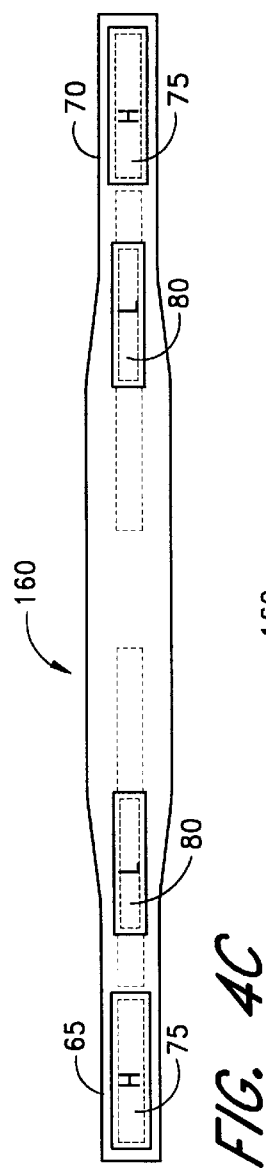
FIG. 4C is an elevational view illustrating the front side of the vertical strap used as part of the second embodiment of the invention.
Figure 4D:
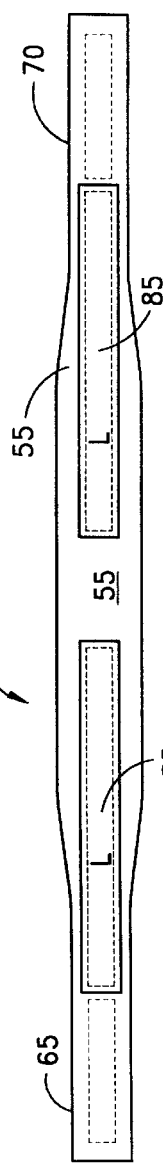
FIG. 4D is an elevational view illustrating the back side of the vertical strap used as part of the second embodiment of the invention.

FIGS. 4C and 4D illustrate the front and back of the vertical strap 160 advantageously used in combination with the horizontal strip 110. As shown, this strap 160 may be the same as the vertical strap 20 described above and having end fasteners 75 made of hook material and middle fasteners 80 made of loop type material.

The side of the vertical strap 160 illustrated in FIG. 4D further includes thermal pack fasteners 85. In the embodiment shown, the thermal pack fasteners 85 are loop fasteners.

FIG. 5 illustrates the retainer member comprising the horizontal and vertical straps, 110 and 160, on the patient's head, in their operative position. As shown, the horizontal strap 110 attaches around the upper portion and over the forehead of the user head with the terry cloth pile facing the patient. The horizontal strap 110 is secured by fastening the left and right fasteners, 140 and 145, together. The vertical strap 160 threads between the user's head and a portion of the horizontal strap 110 on the left side of the user. The left end 65 then folds over the horizontal strap 110. Because the end fastener 75 comprises hook material, the end fastener 75 may attach to both the middle fastener 80 of the vertical strap 160 and fastener 150 of the horizontal strap. The chin area wraps around the user's chin and the right end 70 of the vertical strap 160 attaches in a similar manner to that described with reference to the left end 65.

A feature of both of the preferred embodiments of the invention is that because the cloth strip 55 includes the slightly smaller end widths, that portion of the vertical strap 160 which is under the horizontal strap 110, i.e., between strap 110 and the patient's head, is non-obtrusive to the wearer. Also, it will be understood that a skilled artisan would recognize a wide variety of other ways the vertical strap 20 could attach to the horizontal strap 10. For example, hook material could be attached to the left and right ends, 65 and 70, of the vertical strap 20 on the side facing the user's head. This hook material could then be directly attached to the loop material of the horizontal bag fastener 50 of the horizontal strap 10.

The retainer member in the embodiments described above advantageously provides a lightweight, washable, comfortable, secure anchor for multiple thermal treatment packs 30. For example, as shown in FIGS. 3 and 5, a first and second thermal treatment pack, 100 and 105 of different size and shape constructed in accordance with the treatment pack 30 of FIG. 1D, can be attached in a wide variety of locations. According to one embodiment, the first thermal treatment pack 100 and its fastener strip 98 have a length approximately equal to the length of the vertical strap 20 on the right side of the wearer. As shown in FIG. 3, strip 98 of the first thermal treatment pack 100 advantageously fastens to the vertical bag fasteners 85 on the back side of the vertical strap 20, i.e., between the strap 20 and the user's face. The fastener strip 98 of pack 100 (hook material) fastens to the fastener 85 (loop material) on the vertical strip 20.

As mentioned above, according to another embodiment of the invention, the fasteners 85 on the inner side of vertical strap 20 or 160 are not included. Thus, in this embodiment, only the cloth strip 55 of the vertical strap 20 or 120 is in contact with the user's head. In this embodiment, the first thermal treatment pack 100 may attach to the outwardly exposed middle fasteners 80 of the vertical strap 20 such that the first thermal treatment pack 100 attaches on the side of the vertical strap 20 opposite the user's head, as shown in FIG. 3.

Alternatively, the thermal treatment pack 100 may be retained in the manner of FIG. 5 in which the pack 100 is sufficiently compressed by the vertical strap 160 to be retained between the inside surface of strip 160 and the patient's face.

The second thermal pack 105 has a length along the horizontal strip 10 approximately equal to one half of the frontal area of the user's face. The fastener strip 98 of this second thermal pack 105 fastens to the horizontal bag fastener 50 of horizontal straps 10 or to horizontal bag fastener 150 of horizontal strap 110. Although for purposes of illustration, only first and second thermal treatment packs, 100 and 105, are shown in FIGS. 3 and 5, it will be understood that one to a plurality of thermal treatment packs 30 can be simultaneously fastened to the retainer member. A single or a plurality of thermal treatment packs 30 can be fastened to the retainer member in a wide variety of configurations. Such flexibility in configurations advantageously allows for both complete and partial facial coverage. Further, when the temperature of the cold thermal treatment packs 30 rises, any or all of the thermal treatment packs 30 can be selectively or entirely quickly removed or changed without removing or substantially disturbing the retainer apparatus.

Figure 6:
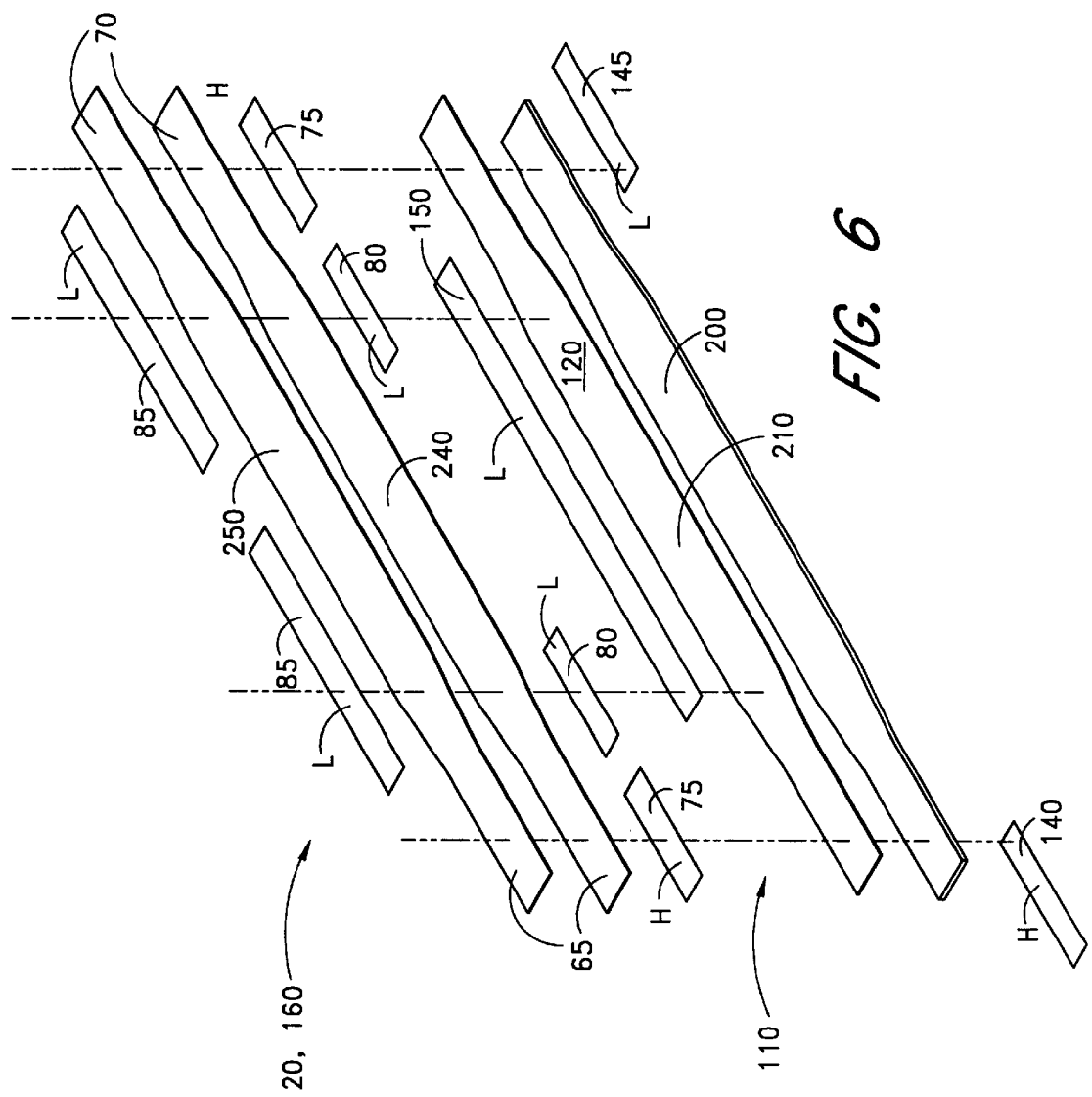
FIG. 6 is an exploded view of individual pieces used to construct the horizontal and vertical straps shown in FIGS. 4A–4D.

FIGS. 4E, 4F and 6 illustrate the preferred method of manufacturing the horizontal and vertical straps. For both the horizontal and vertical straps, two individual cloth strips are attached together, advantageously by placing one strip on top of the other and sewing the two layers together along their entire length proximate to their respective edges shown. As seen in FIG. 4E, a substantially enlarged cross-sectional view of terry cloth strip 200 and plain cloth strip 210 are shown after being sewn together longitudinally at 225, 226. For purposes of both this illustration and FIG. 4F, the space 230 between the inner walls of strips 200 and 210 is exaggerated since the inner walls of the strips 200 and 210 will normally be in close contact with each other. The sewed together strips 200, 210 are then folded inside out (in the same manner that a stocking can be folded inside out) so that the sewing threads 225, 226 are now inside the resulting "tube" formed by the two layers of material and thus concealed and not visible at the outside of the straps, as illustrated by the cross-sectional FIG. 4F.

Likewise, in a similar manner, individual cloth strips 240, 245 are first sewn together and turned inside out to form the vertical strip 160 of FIGS. 4C and 4D or vertical strap 20 of FIGS. 1B and 1C.

Advantageously, in a similar manner, the horizontal strap 10 of FIG. 1A is fashioned from two individual strips of cloth. In the FIG. 1A embodiment, the two strips may be cut from the same cloth.

The dual layer construction provides vertical and horizontal straps which are both soft to the skin and pliable to comfortably conform to the shape of the individual head circumference. As shown in FIG. 4F, the longitudinal edges of the strap have a naturally rounded configuration by virtue of turning the sewn cloth layers inside out, so that the straps are more comfortable to wear than a single thicker layer of cloth. The double layer also provides additional strength and durability.

Another advantage of the double layer construction, particularly with the terry cloth in the second embodiment, is that the straps are able to absorb body fluids such as sweat and saline.

It will be understood that a skilled artisan would recognize a variety of other devices could be attached to the secure retainer apparatus through use of corresponding fastener materials. For example, bandages and the like can advantageously attach to retainer apparatus with or without the thermal treatment packs 30. Another example is that a thermal treatment bag as described above with the fastener strips 98 located along both the top and side of the transparent bag 90 provides for fastening to both the horizontal and vertical straps so as to further secure the thermal treatment pack 30 in place on the patient's face.

The retainer member thus advantageously provides a sturdy, non-intrusive anchor for the treatment packs 30. Placement of the thermal treatment packs 30 can be precisely and sturdily fastened. Retainer apparatus constructed in accordance with the preferred embodiments facilitates user mobility by both allowing for partial facial coverage and allowing for secure placement of the thermal treatment packs 30.

The preferred embodiments of the invention as described above provide several significant features and advantages:

1. The lightweight washable cloth strips form a retainer member that is non-restrictive to the patient. This retainer does not need not be removed when changing or replacing thermal treatment bags fastened to the retainer member.

2. The lightweight washable cloth strips have hook-and-loop fasteners running approximately the entire length of each strip. The hook-and-loop fasteners connect to the thermal treatment bags, thus facilitating easy positioning in a multitude of facial locations while providing stability for the thermal treatment bags when a patient must recuperate in an upright position.

3. The lightweight washable cloth strips cover only a small portion of the patient's head and do not block or limit the area of the patient's face which can be thermally treated.

4. The retainer member allows for selective fastening of multiple thermal treatment bags so as to enable both complete and partial facial coverage from different horizontal and vertical positions.

5. The thermal cold treatment bags advantageously use a multitude of readily available thermal sources. For example, frozen peas provide both the desired cooling temperature and desired immediate molding to a treated area, and also are light in weight compared to other thermal sources.

Although the foregoing invention has been described in terms of certain preferred embodiments, other embodiments will be apparent to those of ordinary skill in the art. For example, the thermal treatment packs 30 could contain warm or hot thermal sources. In addition, the retainer apparatus could be adapted to secure treatment to any area of the human body or even areas of non-human substances or tissues, or the like.

It will also be understood that a skilled artisan could use a wide variety of fasteners in a wide variety of areas on the disclosed retainer apparatus without altering the core advantages disclosed herein. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

I claim:

1. A thermal treatment pack and retainer that provides for a very flexible apparatus that can be easily configured in a plurality of ways to provide thermal treatment for any region of the face comprising:
   a first retainer member formed from a lightweight cloth strip and easily mounted over the patient's forehead in a generally horizontal plane;
   a substantially continuous strip of loop fasteners attached to said first retainer member along an extended length thereof to extend substantially across the patient's forehead;
   a second retainer member formed from a lightweight cloth strip and easily mounted to a patient's head in a generally vertical plane around the chin of the patient;
   a substantially continuous strip of loop fasteners attached to said second retainer member along an extended length thereof to extend substantially the entire distance from the forehead on one side of the face, around the patient's chin and to the forehead on the opposite side of the face;
   a plurality of thermal treatment packs; and
   a plurality of hook fasteners attached to said thermal treatment packs so that said thermal treatment packs can be easily and quickly fastened to said loop fasteners attached to said first and second retainer members to cover any desired region of the patient's facial area and remain in position during normal movement of the patient's head.

2. The thermal treatment pack and retainer of claim 1, wherein said first retainer member has generally smooth front and back cloth surfaces.

3. The thermal treatment pack and retainer of claim 1, wherein said first retainer member has a cloth pile back surface and a generally smooth front cloth surface.

4. The thermal treatment pack and retainer of claim 1, wherein said first retainer member is formed by sewing lengthwise two cloth strips to each other proximate their respective edges and then turning inside out said sewn together cloth strips to conceal the sewing threads.

5. The thermal treatment pack and retainer of claim 1, wherein said second retainer member is formed by sewing lengthwise two cloth strips to each other proximate their respective edges and then turning inside out said sewn together cloth strips to conceal the sewing threads.

6. The thermal treatment pack and retainer of claim 1, wherein both of said first and second retainer members are formed by sewing lengthwise two cloth strips to each other proximate their respective edges and then turning inside out said sewn together cloth strips to conceal the sewing threads.

7. A thermal treatment pack and retainer that provides for a very flexible apparatus that can be easily configured to provide thermal treatment for any region of the face comprising:
   a first retainer member easily mounted to a patient's head in a generally first plane;
   a plurality of loop fasteners attached to one side of said first retainer member along a substantial portion of the length of said first retainer member;
   a second retainer member easily mounted to a patient's head generally in a second plane generally orthogonal to said first plane;
   a plurality of loop fasteners attached on both sides of said second retainer member along a substantial portion of the length of said second retainer member;
   a plurality of thermal treatment packs; and
   a plurality of hook fasteners attached to each of said thermal treatment packs so that said thermal treatment packs can be easily and quickly attached to loop fasteners attached to said first and second retainer members to cover any desired region of the patient's facial area and remain in position during normal movement of the patient's head.

8. A thermal treatment pack and retainer that provides for a very flexible apparatus that can be easily configured to provide thermal treatment for any region of the face comprising:
   a first retainer member easily mounted to a patient's head in a generally first plane;
   a plurality of loop fasteners attached to said first retainer member;
   a second retainer member easily mounted to a patient's head generally in a second plane generally orthogonal to said first plane;
   a plurality of loop fasteners attached to said second retainer member;
   a plurality of thermal treatment packs; and
   a plurality of hook fasteners attached to each of said thermal treatment packs so that said thermal treatment packs can be easily and quickly fastened to loop fasteners attached to said first and second retainer member to cover any desired region of the patient's facial area and remain in position during normal movement of the patient's head;

at least one of said thermal packs having a generally rectangular configuration with a width shorter than the length thereof, said hook fasteners being attached along the width of said thermal pack.

9. A thermal treatment pack and retainer that provides for a very flexible apparatus that can be easily configured in a plurality of ways to provide thermal treatment for any region of the face comprising:

- a first retainer member easily mounted to a patient's head in a generally first plane;
- a plurality of loop fasteners attached to said first retainer member;
- a second retainer member easily mounted to a patient's head generally in a second plane generally orthogonal to said first plane;
- a plurality of loop fasteners attached to said second retainer member;
- a plurality of thermal treatment packs; and
- a plurality of hook fasteners attached to each of said thermal treatment packs so that said thermal treatment packs can be easily and quickly fastened to the loop fasteners attached to said first and second retainer member to cover any desired region of the patient's facial area and remain in position during normal movement of the patient's head;
- at least one of said thermal packs having a generally rectangular configuration with a length longer then the width thereof, said hook fasteners being attached along the length of said thermal pack.

* * * * *